US006171550B1

(12) United States Patent
Bendiner

(10) Patent No.: US 6,171,550 B1
(45) Date of Patent: *Jan. 9, 2001

(54) NON-TOXIC BASE INGREDIENT FOR CONSUMER PRODUCTS

(75) Inventor: Bernard Bendiner, Michigan City, IN (US)

(73) Assignee: Preservation Products, LLC, Michigan City, IN (US)

(*) Notice: Under 35 U.S.C. 154(b), the term of this patent shall be extended for 0 days.

This patent is subject to a terminal disclaimer.

(21) Appl. No.: 08/808,212

(22) Filed: Feb. 28, 1997

(51) Int. Cl.⁷ ............... A61K 7/00; D21C 5/02; D21C 9/00; B01J 19/00
(52) U.S. Cl. ............ 422/28; 424/401; 424/405; 162/5; 162/9; 422/40
(58) Field of Search ............... 424/401, 70.1, 424/405; 422/28, 40; 162/5, 9

(56) References Cited

U.S. PATENT DOCUMENTS

| | | | |
|---|---|---|---|
| 2,703,754 | 3/1955 | Myers | 92/1.6 |
| 3,248,277 | 4/1966 | Gartner | 162/5 |
| 3,808,089 | 4/1974 | Von Koeppen | 162/5 |
| 3,822,178 | 7/1974 | Von Koeppen et al. | 162/5 |
| 4,202,878 | 5/1980 | Ritze | 424/49 |
| 4,570,573 | 2/1986 | Lohman | 119/1 |
| 4,654,207 | 3/1987 | Preston | 424/70 |
| 5,412,090 | 5/1995 | Bendiner | 119/1 |
| 5,491,190 | * 2/1996 | Sandvick et al. | 536/56 |
| 5,840,249 | * 11/1998 | Bendiner | 422/28 |

FOREIGN PATENT DOCUMENTS

| | | |
|---|---|---|
| 131681 | 5/1946 | (AU) . |
| 940250 | 10/1963 | (GB) . |

OTHER PUBLICATIONS

Sato et al, Toothpastes containing granules which change flavor and taste during tooth–brushing. CAPLUS AN 1987:561426 abs., May 28, 1997.*

* cited by examiner

Primary Examiner—Prema Mertz
Assistant Examiner—Joseph F. Murphy
(74) Attorney, Agent, or Firm—Brinks Hofer Gilson & Lione

(57) ABSTRACT

A method for improving products such as toothpaste, shampoo, soap, detergent and lotions or creams by utilizing a water base for the product that is about 99% water, 0.68% cellulose and 0.32% emulsified food grade wax. Products produced with this water base will not decompose even though chemical preservatives is not included as an ingredient. The water base is formed by filtering hydrous cellulose pulp that is resistant to decomposition through a very fine filter. The hydrous cellulose pulp can be produced either by recycling waxed paper or thorough a process that begins with virgin vegetable constituents and wax. The filtrate, or water base can also be used in the horticultural field to prevent mold on plants and in physiology area to prevent the degradation of cells.

8 Claims, No Drawings

NON-TOXIC BASE INGREDIENT FOR CONSUMER PRODUCTS

BACKGROUND OF THE INVENTION

This invention relates to a non-toxic ngredient and the process for producing this ingredient hat can be used as the base in consumer products. When this ingredient is used as the base it is not necessary to add preservatives to the consumer product.

Most paper is made from plant fiber, most often wood, in a process that separates the cellulose from the other plant fiber material. Cellulose, the major constituent of plant fibers, is a carbohydrate. Carbohydrates are convertible into glucose by hydrolysis, a chemical process of decomposition. Under appropriate conditions the bacteria present in the paper making process contributes to and hastens decomposition. As a result, when cellulose pulp material is maintained in a hydrous state it has a very short shelf life.

In the paper making process, water is driven from the cellulose pulp and the remaining fiber is dried in one continuous operation. After the water has been removed, decomposition of the cellulose pulp ceases. However, if the process is suspended with the cellulose pulp in the hydrous state, for example over 90% water, the pulp has a very short shelf life. This short shelf life has been a major obstacle to the development of non-paper industry uses for hydrous cellulose pulp.

Generally speaking, hydrous cellulose pulp is vulnerable to decomposition regardless of whether the pulp is derived from virgin vegetable constituents or from paper in a recycling operation.

Toxic biocides are added to the process during the pulping stage which will inhibit decomposition but not stop it. The introduction of toxic biocides necessitated the addition of safety measures to protect the workers involved in the paper making process. In some paper making processes a slury of hydrous cellulose pulp material is spread in sheets and baled for shipping. Wet lap pulp is the term used to identify this hydrous cellulose pulp material. If biocides are sprayed on the wet lap pulp after it has emerged from the pulper, the toxic biocides escape into the atmosphere and/or flow into our streams and rivers and thus create hazardous conditions. Furthermore, toxic residues remain in the wet lap pulp that may renders it unacceptable for use in consumer products especially consumer products that are consumed. Thus, the toxic biocides must be introduced into the paper making process during the pulping stage rather than being sprayed on the wet lap pulp after it has emerged from the pulping stage. As a result after a batch of wet lap pulp is produced that includes toxic biocides the pulping system must be cleaned to eliminate all biocides residues before a batch of wet lap pulp can be produced that is completely free of toxic biocides.

Waxed paper is customarily manufacture by forming the paper sheet first then treating the sheet with an application of wax coating, either in dry or liquid form. For example, molten paraffin wax is easily applied by continuously passing a paper sheet through a molten bath of wax, removing the excess and then chilling. Such waxed papers have excellent resistance to water vapor, are free from odor, taste and toxicity and are low in cost.

At one time waste waxed paper presented problems in the paper recycling industry. When waste wax paper was recycled waxy spots would appear on the resulting recycled paper and a wax coating would collect on the equipment thus fouling the recycling process.

Consequently, the resulting recycled paper was considered inferior and it was often necessary to stop the process so that the equipment could be adequately cleaned.

This problem, with recycling waste waxed paper, was solved however by adding a water dispersible non-ionic emulsifiers to the pulper during the repulping phase of the recycling process. The mixture containing the emulsifier is mechanically agitated at a temperature sufficiently high to melt the wax, for example from approximately 150° to 190° Fahrenheit. This process produced an emulsified wax-fiber slurry having a solids consistency of from approximately 4% to 6% by weight. The hydrous cellulose pulp produced in this process for recycling waste waxed paper has the property of an unlimited shelf life. U.S. Pat. Nos. 3,808,089 and 3,822,178, the disclosures of which are incorporated herein by reference, fully discloses the above described process.

Various non-paper industry uses have been discovered for this hydrous cellulose pulp having an unlimited shelf life. For example, as a dispersed ingredient in toothpaste, shampoo, soap, detergent, lotions and cream products. Other non-paper industry uses that were discovered for this product were its use as artificial snow and mulch. The discovery of these non-paper industry uses of hydrous cellulose pulp having an unlimited shelf life is the subject matters of U.S. Pat. No. 5,412,090 that issued on May 2, 1995. U.S. Pat. No. 5,412,090 is hereby incorporated by reference as a part of this application. The hydrous cellulose pulp having an unlimited shelf life produced in accordance with the disclosure of U.S. Pat. No. 5,412,090 has a fiber content of about 4–6% by weight. Although this fiber content function, for example when included in shampoo as a scrubbing agent, traces of the fiber that are large enough to be visible to the consumer is left on the hair. This residue, although harmless, is unacceptable to some consumers. For the above reasons there is a need for a hydrous cellulose material that has an unlimited shelf life, that does not leave a visible pulp residue that could render the product in which it is contained unacceptable as a consumer product and is non toxic.

Many consumer products are formed with a water base. The purest natural water includes microorganisms that will in time cause water base products to become rancid if preservatives are not added. Thus, water based consumer products commonly include a preservative. Although preservatives are chosen that most people can tolerate, some individuals are allergic to or have reactions to these preservatives. Also, the long range effect of these preservatives is often not know for certain.

Thus, there is a need for a non toxic product that can server as an exfoliant or emollient agent in consumer products that does not leave a visible residue.

Furthermore, there is a need for a base ingredient that can be used in consumer products that does not require a preservative to prevent the consumer product from degrading and not contaminate the hydrous cellulose material for use in consumer products.

There is also a need in the horticultural field to prevent mold on plants and in physiology area to prevent the degradation of cells.

SUMMARY OF THE INVENTION

It is an object of this invention to utilize hydrous cellulose pulp in a process that will produce a natural base ingredient that includes colloidal cellulose particles that do not require a preservative and can be used as the water base in consumer products.

It is another object of this invention to provide a method for improving toothpaste, shampoo, soap, detergent, lotions and cream products by using a liquid base ingredient that contains about 0.68% colloidal cellulose particles that has an unlimited shelf life and that functions as a natural ingredient preservative for the other ingredients of the product, is not toxic, does not leave a visible residue, and is soft and soothing to the skin or mucous membrane.

It is a further object of this invention to provide a process for improving toothpaste, shampoo, soap, detergent, lotions and cream products that includes the steps of repulping waxed paper in a process requiring an emulsifier and heat sufficient to melt the wax to thus provide a micro-molecular film on the fiber, filter out the fiber, using a 2 micrometer filter and then utilize the filtrate which contains minute wax coated fiber filaments as the water base ingredient in the process for producing non toxic consumer products.

When this filtrate is used for example as the water base for hair spray a molecular film of food grade wax is left on the users hair which makes the hair easier to groom.

It is a further object of this invention to provide a process for producing a water base that has the quality of opacity which can be used as the water base in products such as toothpaste, shampoo, soap, detergent, lotions and cream products. This process includes the steps of repulping waxed paper in a process requiring an emulsifier and heat sufficient to melt the wax to thus provide a micro-molecular film on the fiber resulting from the repulping process, filter out the visible fiber strands, blending the filtrate such that the minute film coated particles become dispersed in the liquid and then utilize the liquid with the dispersed film coated particles as the water base ingredient in consumer products.

It is a still further object of this invention to provide a process for improving water based products such as toothpaste, shampoo, soap, detergent, lotions and cream products by utilizing in the process for forming the product a water base ingredient that is completely free of microorganisms and includes minute particles of fiber dispersed therein that are coated with a thin wax film.

It is an object of this invention to utilize a filtrate of hydrous cellulose pulp that has an unlimited shelf life in a process that will function as a natural ingredient preservative to the other ingredients contained in the process and improve the quality of the product.

It is another object of this invention to provide a method for improving toothpaste, shampoo, soap, detergent lotions and cream products by using a liquid base that contains about 0.68% colloidal cellulose particles and about 0.32% emulsified food grade wax that function as a natural preservative to the other ingredients of the product and does not leave a visible residue.

It is a further object of this invention to provide a process for improving low viscosity products such as mouthwash or glass cleaners that include the steps of forming colloidal cellulose particles that has an unlimited shelf life from natural materials in the presence of wax in a process requiring an emulsifier and heat for increasing the temperature sufficient to melt the wax to thus provide a micromolecular film on the fiber and then blend and filter the hydrous cellulose pulp and utilize the resulting filtrate as the water base ingredient for the low viscosity products.

Another object of this invention is to prevent mold on plants and trees by applying the filtrate as a mulch for and a water source for the plants.

It is yet another object of this invention to use the filtrate to protect healthy cells in animals and humans from attack by cells that have been degraded by cancer, aids and viruses that degrade cells.

DETAILED DESCRIPTION OF THE PREFERRED EMBODIMENT

During the emulsification phase, of the wax paper recycling process used in practicing this invention, and more fully disclosed in the above identified U.S. Pat. No. 5,412,090, substantial quantities of wax are present from the waste waxed paper. However, this wax does not contaminate or coat the equipment even when slurries containing the emulsified product are cooled. When making waxed paper, very little wax penetrates below the surface of the un-waxed sheet of paper. However, during the emulsification phase of recycling, the paper is broken down into minute fiber filaments having irregularly shaped surfaces. Each of these minute filaments has a substantial surface area. Literally millions of fiber filaments are released from a relatively small piece of wax paper. Consequently, a piece of waxed paper having a waxed surface of 100 square inches, for example, releases fiber filaments into the emulsified slurry that have a surface area that may be as much as 1,000,000 times the original 100 square inches, or 10,000,000 square inches. The wax from the surface of the waxed paper, is melted during the emulsification phase and forms a very thin micro-molecular film on the fiber filaments. In addition to the minute fiber filaments there are numerous microorganisms from the water and other ingredients of the recycling process. The microorganisms would in the usual paper making process cause decommission of the process ingredients. However, in the process of this invention these microorganisms becomes coated with a very thin layer of wax which prevents them from causing decommission of other ingredients found in the process. This hydrous cellular pulp is 95% water, 4.67% fiber and 0.32% wax. The hydrous cellular pulp is then filtered through a very fine filter, for example a 2 micrometer (0.000002 meters) filter and the resulting filtrate is then used as the water base in products such as toothpaste, shampoo, soap, detergent, lotions and cream products. This filtrate is 99% water, 0.68 colloidal cellulose particles and 0.32% emulsified food grade wax. A colloidal dispersion is thus formed having colloidal cellulose particles that are smaller than 35 microns. The colloidal cellulose particles are not visible to the naked eye. The filtrate is an emollient which is soothing to the skin or mucous membrane.

This hydrous cellulose pulp and the filtrate thereof is free of microorganisms such as bacteria and fungi, possesses an unlimited shelf life, and may be produced either by recycling waste waxed paper, new waxed paper or by processing virgin vegetable constituents in the presence of wax during the emulsification phase of the defibering process.

A protective barrier is also believed to form around the molecular structure of the water. The filtrate contains minute portions of fiber coated with a thin micro-molecular layer of wax derived from this process is non toxic and has an unlimited shelf life and thus can be utilized as the water base ingredient for consumer products and provide the product with an unlimited shelf life.

The filtrate functions as a water base that is free of biological microorganisms and includes minute portions of fiber that has been coated with a thin micromolecular layer of wax. The minute portions of wax coated fiber function as scrubbing agents in shampoos, soaps and detergents. The resulting product has an unlimited shelf life and is non toxic.

In accordance with this invention, an example of the type of waxed paper that can be used, in the practice of this invention is the type used in bakeries and delicatessens to wrap food products. Waxed paper of this type is coated with a food grade paraffin wax, designated as a dry wax. Waste waxed paper can be used in the preferred embodiment that is obtained directly from the paper producing facilities. For example, trimmings from a trimming machine or wax paper that did not meet required test standards may be used. Such waxed paper is free of printing and thus is clean. The waxed paper is added to a pulper. A pulper is basically a vat for receiving a material that can be agitated by mechanical means and includes means to control the temperature. The process of pulping is essentially one of separating cells from intercellular material. It should be understood that any equipment such as a conventional high speed pulper may be used. The temperature of the wax-containing fiber slurry is raised to a temperature above the melting point of the wax. The slurry is beat until the wax and fiber are released into the aqueous solution. The resulting water-fiber slurry can then be subjected to a washing process to remove any impurities. Newly manufactured waked paper does not need this washing process.

The process of the present invention encompasses the use of 100% waxed paper stock having a wax content of up to 30% by weight. However, non-waxed waste paper, in modest proportions can be used without affecting the outcome. Non waxed fiber products can be used as a starting product and a paraffin wax in the correct ratio to fiber added. The use of waxed paper as a starting point has the advantage that it contains the proper ratio of fiber to wax and it is available at economical rates.

The water soluble non-ionic emulsifier that is added to the slurry being from the group consisting of: polyethylene glycol ethers of hydrophobic alcohols; alkylphenoxy polyethoxyethanols; fatty acid amides and mixtures thereof. The water soluble non-ionic emulsifier must also meet specific emulsion stability standards. The preferred water soluble non-ionic emulsifiers include: ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1; ethoxylated alkyl phenols in which the ratio of moles of ethylene oxide per mole or ethylene oxide per mole of alkyl phenol is in the range of 7–8 inclusive; ethoxylated alkyl phenols in which the alkyl substituent is linear; and the fatty acid amide diethanol amine condensates derived from a member selected from the group consisting of myristic acid, lauric acid, palmitic acid, stearic acid and mixtures thereof.

After the process for producing the hydrous cellulose pulp has been completed, it is filtered through a 2 micrometer filter to remove the larger portions of hydrous cellulose pulp, leaving a filtrate comprised of colloidal cellulose particles that are smaller than 35 microns. This filtrate is free of microorganism and the colloidal cellulose particles are coated with a very thin layer of wax. This filtrate is mixed to suspend the coated fiber in the liquid. This filtrate can then be utilized as the water base ingredient in products such as toothpaste, shampoo, soap, detergent, lotions or creams. Wax from the original waste waxed paper is present on the minute portions of fiber that are dispersed in the final product. However, such wax is present on the minute fibers filaments, in a very thin coating. Although a 2 micrometer filter is used in the preferred embodiment it should be understood that although a very fine filter is necessary it can vary within limits of 2 micrometers.

The filtrate can also be used in the horticulture area. The filtrate is used to mulch or water plants and the wax coated colloidal cellulose particles are synthesized by the roots and work their way up to the leaves. It has been demonstrated that mold that exist on leaves prior to the application of the filtrate does not permeate to the healthy portions of the leaf. The wax coated colloidal cellulose particles forms a molecular film around the plant cells and protects them from attack by the mold.

It is felt that, consistent with known similar situations in the biological field, the results found in the biological plant world will be duplicated in the biological animal world. It is felt, for example, that the wax coated colloidal cellulose particles will be synthesized in animals including humans and a film will be formed around healthy cells that will protect them from attack by cells that have been degraded. Thus, this invention contemplates a process for retarding cellular deterioration in animals, including humans, in which the cells are degrading as a result of cancer, aids or viruses that create cellular degradation such as hepatitis.

While the invention has heretofore been described in detail with particular reference to specific products, it is to be understood that variation, modifications and the use of equivalents can be effected without departing from the scope of this invention. It is, therefore, intended that such changes and modifications be covered by the following claims.

I claim:

1. A process for improving toothpaste, shampoo, soap, detergent and lotions or creams comprising the steps of:
   (a) producing a decomposition resistant hydrous cellulose pulp, the individual fibers of which are coated with a thin wax film; and
   (b) filtering the hydrous cellulose pulp through a fine filter; and
   (c) utilizing the filtrate as the water base in toothpaste, shampoo, soap, detergent and lotions or creams.

2. The invention as set forth in claim 1 wherein said fine filter has openings that are about 2 micrometers in size.

3. The invention as set forth in claim 1 wherein in the process for producing the decomposition resistant hydrous cellulose pulp a water soluble non-ionic emulsifier that meets the following emulsion stability standards is used:
   ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

4. The invention as set forth in claim 2 wherein in the process for producing the decomposition resistant hydrous cellulose pulp a water soluble non-ionic emulsifier that meets the following emulsion stability standards is used:
   ethoxylated aliphatic alcohols wherein the alcohol is a hydrophobic secondary alcohol having from 11 to 15 carbon atoms and wherein the average molar ratio of ethylene oxide to hydrophobic alcohol is in a range of 5:1 to 15:1.

5. The invention as set forth in claim 1 wherein in the process for producing the decomposition resistant hydrous cellulose pulp a water soluble non-ionic emulsifier that meets the following emulsion stability standards is used:
   ethoxylated alkyl phenols in which the ratio of moles of ethylene oxide per mole or ethylene oxide per mole of alkyl phenol is in the range of 7–8 inclusive.

6. The invention as set forth in claim 2 wherein in the process for producing the decomposition resistant hydrous cellulose pulp a water soluble non-ionic emulsifier that meets the following emulsion stability standards is used:
   ethoxylated alkyl phenols in which the ratio of moles of ethylene oxide per mole or ethylene oxide per mole of alkyl phenol is in the range of 7–8 inclusive.

7. The invention as set forth in claim 1 wherein in the process for producing the decomposition resistant hydrous cellulose pulp a water soluble non-ionic emulsifier that meets the following emulsion stability standards is used:
   ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

8. The invention as set forth in claim 2 wherein in the process for producing the decomposition resistant hydrous cellulose pulp a water soluble non-ionic emulsifier that meets the following emulsion stability standards is used:
   ethoxylated alkyl phenols in which the alkyl substituent is linear and the fatty acid amide diethanol amine condensates derived from a member selected from the group consisting of myristic acid, lauric acid, palmitic acid, stearic acid and mixtures thereof.

* * * * *